(12) United States Patent
Okumura et al.

(10) Patent No.: US 7,230,057 B2
(45) Date of Patent: Jun. 12, 2007

(54) BORON-CONTAINING COMPOUND, ION-CONDUCTIVE POLYMER AND POLYELECTROLYTE FOR ELECTROCHEMICAL DEVICES

(75) Inventors: Takefumi Okumura, Hitachi (JP); Shin Nishimura, Hitachi (JP); Norio Iwayasu, Hitachinaka (JP); Shoichi Yokoyama, Yokohama (JP); Takeshi Yabe, Kawasaki (JP)

(73) Assignees: Hitachi, Ltd., Tokyo (JP); NOF Corporation, Tokyo (JP)

( * ) Notice: Subject to any disclaimer, the term of this patent is extended or adjusted under 35 U.S.C. 154(b) by 554 days.

(21) Appl. No.: 10/717,645

(22) Filed: Nov. 21, 2003

(65) Prior Publication Data
US 2004/0147697 A1 Jul. 29, 2004

(30) Foreign Application Priority Data
Nov. 21, 2002 (JP) ............................. 2002-337789

(51) Int. Cl.
C08F 130/06 (2006.01)
C07F 5/04 (2006.01)
(52) U.S. Cl. ...................... 526/239; 558/293; 429/309; 429/317; 429/322
(58) Field of Classification Search ................ 429/309, 429/317, 322; 526/239; 558/293
See application file for complete search history.

(56) References Cited
U.S. PATENT DOCUMENTS 3,697,575 A 10/1972 Naarmann et al.
3,743,686 A 7/1973 Koch et al.

6,833,220 B1* 12/2004 Yokoyama et al. ......... 429/317

FOREIGN PATENT DOCUMENTS

EP 1 160 268 12/2001
EP 1160268 A1 * 12/2001

(Continued)

Primary Examiner—David W. Wu
Assistant Examiner—M. Bernshteyn
(74) Attorney, Agent, or Firm—Antonelli, Terry, Stout & Kraus, LLP.

(57) ABSTRACT

An object of the present invention is to provide a boron-containing compound capable of forming an ion-conductive polyelectrolyte having high ion-conductive properties, and a polymer of said compound. According to the present invention, there are provided a polymerizable boron-containing compound of (formula 1), a polymer thereof, a polymer of a compound of (formula 2) and a compound of (formula 3), and a polyelectrolyte for electrochemical device comprising either of these polymers and at least one electrolyte salt:

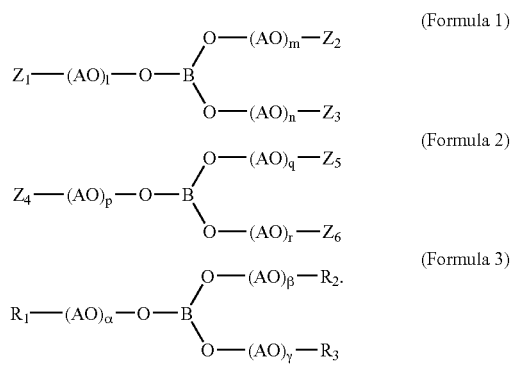

10 Claims, 1 Drawing Sheet

FOREIGN PATENT DOCUMENTS

| | | |
|---|---|---|
| JP | 48-60183 | 8/1973 |
| JP | 61-215610 | 9/1986 |
| JP | 62-201913 | 9/1987 |
| JP | 2001-72875 | 3/2001 |
| JP | 2001-72876 | 3/2001 |
| JP | 2001-72877 | 3/2001 |
| JP | 2001-72878 | 3/2001 |
| JP | 2002-158039 | 5/2002 |
| SU | 1730091 | 4/1992 |
| WO | WO 200139316 A1 * | 5/2001 |
| WO | WO 03/031453 | 4/2003 |

* cited by examiner

FIG.1

BORON-CONTAINING COMPOUND, ION-CONDUCTIVE POLYMER AND POLYELECTROLYTE FOR ELECTROCHEMICAL DEVICES

BACKGROUND OF THE INVENTION

The present invention relates to a boron-containing compound, a polymerizable composition and an ion-conductive polyelectrolyte which are for electro-chemical devices.

As an electrolyte that constitutes an electro-chemical device such as a battery, capacitor, sensor or the like, a liquid electrolyte has been used from the viewpoint of ion-conductive properties. The liquid electrolyte, however, has been disadvantageous, for example, in that its leakage tends to damage an apparatus.

On the other hand, secondary batteries using a solid electrolyte such as an inorganic crystalline material, inorganic glass, organic polymer or the like have recently been proposed. As compared with the employment of a conventional liquid electrolyte obtained by the use of a carbonate solvent, the employment of the solid electrolyte is free from the leakage of the carbonate solvent and permits reduction of the ignitability of the electrolyte, so that it improves the reliability and safety of a device.

Organic polymers are expected to be developed, for example, because in general, they are excellent in processability and moldability, give an electrolyte having flexibility and processability in bending, and improve the degree of freedom of design of a device obtained by the use of the organic polymer.

The organic polymers described above, however, are inferior to other materials in ion-conductive properties. There is widely known, for example, an attempt to use a material obtained by incorporating a poly(ethylene oxide) with a specific alkali metal salt, as a polyelectrolyte (for instance, JP-A-2002-158039).

JP-A-2001-72877 discloses a copolymer of a boron-containing polymerizable monomer and another polymerizable monomer. This polymer is an ion-conductive material capable of improving the transference number of charge carriers, and the above reference discloses a polyelectrolyte and an electrochemical device which are obtained by the use of said polymer.

However, even when the polyelectrolyte concretely described in the above reference is used, no ionic conductivity value required, in practice, of an electrolyte for a lithium ion secondary battery is obtained.

SUMMARY OF THE INVENTION

The present invention was made in view of such conditions and is intended to provide a novel boron-containing compound and a novel boron-containing ion-conductive polyelectrolyte that has both a high safety and a high ionic conductivity.

The present invention provides a boron-containing compound represented by (formula 1) and an ion-conductive polyelectrolyte:

(Formula 1)

wherein B is a boron atom; $Z_1$, $Z_2$ and $Z_3$ are independently an organic group having an acryloyl or methacryloyl group, or a hydrocarbon group of 1 to 10 carbon atoms, provided that one or two of $Z_1$, $Z_2$ and $Z_3$ are organic groups having an acryloyl or methacryloyl group; AOs are independently an oxyalkylene group of 1 to 6 carbon atoms and are of one or more kinds; and l, m and n are independently an average number of moles of the oxyalkylene group(s) added of less than 4 and more than 0, provided that l+m+n is 1 or more.

The present invention also provides a polymerizable composition of boron-containing compounds represented by (formula 2) and (formula 3), respectively, and an ion-conductive polyelectrolyte:

(Formula 2)

(Formula 3)

wherein B is a boron atom; $Z_4$, $Z_5$ and $Z_6$ are independently an organic group having an acryloyl or methacryloyl group, or a hydrocarbon group of 1 to 10 carbon atoms, provided that at least one of $Z_4$, $Z_5$ and $Z_6$ is an organic group having an acryloyl or methacryloyl group; $R_1$, $R_2$ and $R_3$ are independently a hydrocarbon group of 1 to 10 carbon atoms; AOs are independently an oxyalkylene group of 1 to 6 carbon atoms and are of one or more kinds; and p, q, r, $\alpha$, $\beta$ and $\gamma$ are independently an average number of moles of the oxyalkylene group(s) added of less than 4 and more than 0, provided that each of the sum p+q+r and the sum $\alpha+\beta+\gamma$ is 1 or more.

When an ion-conductive polyelectrolyte comprising a polymer obtained by polymerizing a compound or composition within the scope of the present invention is used, the number of moles of the added oxyalkylene group(s) is small, so that lithium ions coordinating with the ether oxygen(s) can easily move, resulting in a high ionic conductivity.

Other objects, features and advantages of the invention will become apparent from the following description of the embodiments of the invention taken in conjunction with the accompanying drawings.

BRIEF DESCRIPTION OF DRAWING

In FIG. 1, the symbols denote the following.
1: Positive electrode; 2: negative electrode; 5: positive electrode terminal made of stainless steel; 6: negative electrode terminal made of stainless steel; 7: aluminum laminate film.

DETAILED DESCRIPTION OF THE INVENTION

The present invention is explained below in detail.

The compounds of (formula 1), (formula 2) and (formula 3) according to the present invention have one or more oxyalkylene groups of 1 to 6 carbon atoms. As the oxyalkylene group(s) in the molecule, one or more kinds of oxyalkylene groups may be used.

The oxyalkylene group(s) includes, for example, oxyethylene group, oxypropylene group, oxybutylene group and oxytetramethylene group. The oxyalkylene group(s) is preferably that having 2 to 4 carbon atoms, in particular, oxyethylene group or oxypropylene group.

One or two of $Z_1$, $Z_2$ and $Z_3$ in (formula 1) are organic groups having an acryloyl or methacryloyl group, and the one or two others are hydrocarbon groups of 1 to 10 carbon atoms.

Each of $Z_4$, $Z_5$ and $Z_6$ in (formula 2) is an organic group having an acryloyl or methacryloyl group, or a hydrocarbon group of 1 to 10 carbon atoms. One or more, preferably all, of them are organic groups having an acryloyl or methacryloyl group.

The organic group having an acryloyl or methacryloyl group is that having an acryloyl or methacryloyl group at the end. Preferable examples thereof are acryloyl group and methacryloyl group. An electrolyte goodness in electrical characteristics and handleability can be obtained by keeping the organic group(s) having a polymerizable double bond, in the scope of the present invention.

Each of $R_1$, $R_2$ and $R_3$ in (formula 3) is a hydrocarbon group of 1 to 10 carbon atoms. The number of carbon atoms of the hydrocarbon group is 1 to 10, and the hydrocarbon group includes, for example, aliphatic hydrocarbon groups such as methyl, ethyl, propyl, butyl, pentyl, hexyl, heptyl, octyl, nonyl, decyl, etc.; aromatic hydrocarbon groups such as phenyl, toluyl, naphthyl, etc.; and alicyclic hydrocarbon groups such as cyclopentyl, cyclohexyl, methylcyclohexyl, dimethylcyclohexyl, etc. As said hydrocarbon group, hydrocarbon groups of 4 or less carbon atoms are preferable, and methyl group having one carbon atom is especially preferable.

Each of l, m and n in (formula 1) is an average number of moles of added oxyalkylene group(s). Each of l, m and n is less than 4 and more than 0, preferably 1 to 3. The sum l+m+n is 1 or more, preferably 3 to 9.

Each of p, q, r, $\alpha$, $\beta$ and $\gamma$ in (formula 2) and (formula 3) is an average number of moles of added oxyalkylene group(s). Each of p, q, r, $\alpha$, $\beta$ and $\gamma$ is less than 4 and more than 0, preferably 1 to 3. Each of the sum p+q+r and the sum $\alpha$+$\beta$+$\gamma$ is 1 or more, preferably 3 to 9.

Each of the boron-containing compounds of (formula 1), (formula 2) and (formula 3) can be produced by either a well-known process or the following process. Each boron-containing compound can be obtained by adding a boron compound such as boric acid, boric anhydride, alkyl borate or the like to an oxyalkylene compound having a hydroxyl group, and carrying out boric acid esterification at 50 to 200° C. under reduced pressure while introducing a dry gas. The boron-containing compound is produced, for example, by carrying out the esterification with stirring for 2 to 12 hours at a reaction temperature of 60 to 120° C. while introducing a proper amount of dry air, and carrying out dehydration or elimination of a volatile matter under a reduced pressure of 1.33 to 66.7 kPa (10 to 500 mmHg). Considering, in particular, the reduction of the water content and the like, the boron-containing compound is preferably produced by using a trialkyl borate, in particular, trimethyl borate. Particularly when a trialkyl borate is used, the boron-containing compound is preferably produced by using the trialkyl borate in an amount of 1.0 mol to 10 mols per 3.0 mols of an oxyalkylene compound having a hydroxyl group, and distilling off the volatile matter produced by the boric acid transesterification and the excess trialkyl borate.

As to the mixing ratio between the compound of (formula 2) and the compound of (formula 3), the molar ratio [(the number of moles of the compound of (formula 3))/(the number of moles of the compound of (formula 2))] is 0.1 to 9, preferably 0.5 to 4, more preferably 0.5 to 3, in particular, 1 to 2.5. When the molar ratio is less than 0.1, the mechanical strength is increased and the flexibility is deteriorated, so that shaping of an electrolyte membrane becomes difficult. When the molar ratio is more than 9, the mechanical strength is decreased, and formation of the solid polyelectrolyte is difficult. When the molar ratio is more than 4, the mechanical strength is decreased, resulting in difficult handling.

When the molar ratio [(the number of moles of the compound of (formula 3))/(the number of moles of the compound of (formula 2))] is 4–9, the molecules move actively with their geometry maintained and ionic conductivity is increased though the mechanical strength is decreased, resulting in difficult handling.

Each of a polymer of the boron-containing compound of (formula 1) and a polymer of a mixture of the compound of (formula 2) and the compound of (formula 3) can be obtained by a well-known process. It is possible to use, for example, the energy of visible light, ultraviolet light, electron beams, heat or the like, and optionally a polymerization initiator and the like. Each of the above-mentioned polymers can be obtained by either ionic polymerization or radical polymerization.

In the present invention, a polymerization initiator may be or need not be used for producing the polymer from the boron-containing compound of (formula 1) or a mixture of the boron-containing compounds of (formula 2) and (formula 3). Thermal radical polymerization using a free-radical initiator is preferable from the viewpoint of work efficiency and polymerization rate.

The free-radical initiator includes organic peroxides such as t-butyl peroxypivalate, t-hexyl peroxypivalate, methyl ethyl ketone peroxide, cyclohexanone peroxide, 1,1-bis(t-butylperoxy)-3,3,5-trimethylcyclohexane, 2,2-bis(t-butylperoxy)octane, n-butyl-4,4-bis(t-butylperoxy)-valerate, t-butyl hydroperoxide, cumene hydroperoxide, 2,5-dimethylhexane-2,5-dihydroperoxide, di-t-butyl peroxide, t-butylcumyl peroxide, dicumyl peroxide, $\alpha,\alpha'$-bis(t-butylperoxy-m-isopropyl)benzene, 2,5-dimethyl-2,5-di(t-butylperoxy)hexane, benzoyl peroxide, t-butyl peroxyisopropyl carbonate, etc.; and azo compounds such as 2,2'-azobisisobutyronitrile, 2,2'-azobis(2-methylbutyronitrile), 2,2'-azobis(4-methoxy-2,4-dimethylvaleronitrile), 2,2'-azobis(2,4-dimethyl-valeronitrile), 1,1'-azobis(cyclo-hexane-1-carbonitrile), 2-(carbamoylazo)isobutyronitrile, 2-phenylazo-4-methoxy-2,4-dimethyl-valeronitrile, 2,2'-azobis(2-methyl-N-phenylpropionamidine) dihydrochloride, 2,2'-azobis[N-(4-chlorophenyl)-2-methylpropionamidine] dihydrochloride, 2,2'-azobis[N-hydroxyphenyl-2-methylpropionamidine] dihydrochloride, 2,2'-azobis[2-methyl-N-(phenylmethyl)propionamidine] dihydrochloride, 2,2'-azobis[2-methyl-N-(2-propenyl)-propionamidine] dihydrochloride, 2,2'-azobis(2-methylpropionamidine) dihydrochloride, 2,2'-azobis[N-(2-hydroxyethyl)-2-methylpropionamidine] dihydrochloride, 2,2'-azobis[2-(5-methyl-2-imidazolin-2-yl)propane] dihydrochloride, 2,2'-azobis[2-

(2-imidazolin-2-yl)propane] dihydrochloride, 2,2'-azobis[2-(4,5,6,7-tetrahydro-1H-1,3-diazepin-2-yl)propane] dihydrochloride, 2,2'-azobis[2-(3,4,5,6-tetrahydropyrimidin-2-yl)propane] dihydrochloride, 2,2'-azobis[2-(5-hydroxy-3,4,5,6-tetrahydropyrimidin-2-yl)propane] dihydrochloride, 2,2'-azobis{2-[1-(2-hydroxyethyl)-2-imidazolin-2-yl]propane} dihydrochloride, 2,2'-azobis[2-(2-imidazolin-2-yl)propane], 2,2'-azobis{2-methyl-N-[1,1-bis(hydroxymethyl)-2-hydroxyethyl]propionamide}, 2,2'-azobis{2-methyl-N-[1,1-bis(hydroxymethyl)ethyl]propionamide}, 2,2'-azobis[2-methyl-N-(2-hydroxyethyl)propionamide], 2,2'-azobis(2-methylpropionamide) dihydrate, 2,2'-azobis(2,4,4-trimethylpentane), 2,2'-azobis(2-methylpropane), dimethyl 2,2'-azobisisobutyrate, 4,4'-azobis(4-cyanovaleric acid), 2,2'-azobis[2-(hydroxymethyl) propionitrile], etc.

The production of the polymer by the use of the free-radical initiator can be carried out in a conventional temperature range by employing a conventional polymerization time.

In order to prevent damage to members used in an electrochemical device, there is preferably used a free-radical initiator whose 10-hours half-life temperature range as an indication of decomposition temperature and rate is 30 to 90° C. The proportion of the initiator in the present invention is not more than 10 mol % and not less than 0.01 mol %, preferably not more than 5 mol % and not less than 0.1 mol %, based on the amount of the above-mentioned polymerizable functional group(s).

In the present invention, any electrolytic salt may be used so long as it is soluble in the boron-containing compound having at least one oxyalkylene group of the present invention or a polymer of said compound. Preferable examples of the electrolytic salt are compounds composed of a metal cation and an anion selected from chlorine ion, bromine ion, iodine ion, perchlorate ion, thiocyanate ion, tetrafluoroborate ion, hexafluorophosphate ion, trifluoromethanesulfonidimidate ion, stearylsulfonate ion, octylsulfonate ion, dodecylbenzenesulfonate ion, naphthalenesulfonate ion, dodecylnaphthalenesulfonate ion, 7,7,8,8-tetracyano-p-quinodimethane ion and lower aliphatic carboxylate ions. The metal cation includes Li, Na, K, Rb, Cs, Mg, Ca and Ba metal ions. As to the concentration of the electrolytic salt relative to the total number of moles of ether oxygen atoms in oxyalkylene groups in the ion-conductive polymer, the molar-ratio [(the number of moles of the electrolytic salt)/(the total number of moles of ether oxygen atoms in the oxyalkylene groups)] ranges preferably from 0.0001 to 1, preferably from 0.001 to 0.5. When the molar ratio is more than 1, the processability, the moldability and the mechanical strength of the resulting polyelectrolyte are deteriorated.

The polyelectrolyte of the present invention is useful particularly as an electrolyte for secondary battery.

DESCRIPTION OF THE PREFERRED EMBODIMENTS

The present invention is more concretely illustrated with reference to the following examples, which should not be construed as limiting the scope of the invention. In the examples, sample preparation and ionic conductivity evaluation were carried out under an argon atmosphere unless otherwise specified. In each example and each comparative example, the concentration of an electrolytic salt blended relative to the total number of moles of ether oxygen atoms in oxyalkylene groups in an ion-conductive polymer was adjusted so that the molar ratio [(the number of moles of the electrolytic salt)/(the total number of moles of ether oxygen atoms in the oxyalkylene groups)] might be 0.125. Table 1 lists the examples and comparative examples of the present invention.

TABLE 1

| Example | Number of moles of compound of (formula 1) (mmol) | Number of moles of compound of (formula 2) (mmol) | Number of moles of compound of (formula 3) (mmol) | Number carbon of atoms in oxyalkylene group | | | Electrolytic salt | | |
|---|---|---|---|---|---|---|---|---|---|
| | | | | 4 | 3 | 2 | $LiBF_4$ | $LiPF_6$ | $LiN(CF_3SO_2)_2$ |
| 1 | 10 | — | — | ○ | — | — | ○ | — | — |
| 2 | 10 | — | — | ○ | — | — | — | ○ | — |
| 3 | 10 | — | — | ○ | — | — | — | — | ○ |
| 4 | 10 | — | — | — | ○ | — | ○ | — | — |
| 5 | 10 | — | — | — | ○ | — | — | ○ | — |
| 6 | 10 | — | — | — | ○ | — | — | — | ○ |
| 7 | 10 | — | — | — | — | ○ | ○ | — | — |
| 8 | 10 | — | — | — | — | ○ | — | ○ | — |
| 9 | 10 | — | — | — | — | ○ | — | — | ○ |
| 10 | — | 10 | 10 | ○ | — | — | ○ | — | — |
| 11 | — | 10 | 10 | ○ | — | — | — | ○ | — |
| 12 | — | 10 | 10 | ○ | — | — | — | — | ○ |
| 13 | — | 10 | 10 | — | ○ | — | ○ | — | — |
| 14 | — | 10 | 10 | — | ○ | — | — | ○ | — |
| 15 | — | 10 | 10 | — | ○ | — | — | — | ○ |
| 16 | — | 10 | 10 | — | — | ○ | ○ | — | — |
| 17 | — | 10 | 10 | — | — | ○ | — | ○ | — |
| 18 | — | 10 | 10 | — | — | ○ | — | — | ○ |
| 19 | — | 10 | 20 | ○ | — | — | ○ | — | — |
| 20 | — | 10 | 20 | ○ | — | — | — | ○ | — |
| 21 | — | 10 | 20 | ○ | — | — | — | — | ○ |
| 22 | — | 10 | 20 | — | ○ | — | ○ | — | — |
| 23 | — | 10 | 20 | — | ○ | — | — | ○ | — |
| 24 | — | 10 | 20 | — | ○ | — | — | — | ○ |

TABLE 1-continued

| Example | Number of moles of compound of (formula 1) (mmol) | Number of moles of compound of (formula 2) (mmol) | Number of moles of compound of (formula 3) (mmol) | Number carbon of atoms in oxyalkylene group | | | Electrolytic salt | | |
|---|---|---|---|---|---|---|---|---|---|
| | | | | 4 | 3 | 2 | LiBF$_4$ | LiPF$_6$ | LiN(CF$_3$SO$_2$)$_2$ |
| 25 | — | 10 | 20 | — | — | ○ | ○ | — | — |
| 26 | — | 10 | 20 | — | — | ○ | — | ○ | — |
| 27 | — | 10 | 20 | — | — | ○ | — | — | ○ |
| Comparative Example 1 | — | — | — | — | — | — | — | — | — |
| Comparative Example 2 | — | — | — | — | — | — | — | — | — |

1. Examples of Preparation of Electrodes:

(Positive electrode): CELLSEED (lithium cobaltate manufactured by Nippon Chemical Industrial Co., Ltd.), SP270 (graphite manufactured by Japan Graphite Co., Ltd.) and KF1120 (polyvinylidene fluoride manufactured by Kureha Chemical Industry Co., Ltd.) were mixed at a ratio of 80:10:10 in % by weight, and the mixture was introduced into N-methyl-2-pyrrolidone, followed by mixing to prepare a slurry solution. The resulting slurry was coated on an aluminum foil of 20 µm in thickness by doctor blade method and dried. The coating amount of the mixture was 150 g/m$^2$. The aluminum foil was pressed to give a mixture bulk density of 3.0 g/cm$^3$, and cut to 1 cm×1 cm to prepare a positive electrode.

(Negative electrode): CARBOTRON PE (amorphous carbon manufactured by Kureha Chemical Industry Co., Ltd.) and KF1120 (polyvinylidene fluoride manufactured by Kureha Chemical Industry Co., Ltd.) were mixed at a ratio of 90:10 in % by weight, and the mixture was introduced into N-methyl-2-pyrrolidone, followed by mixing to prepare a slurry solution. The resulting slurry was coated on a copper foil of 20 µm in thickness by doctor blade method and dried. The coating amount of the mixture was 70 g/m$^2$. The copper foil coated with the slurry was pressed to give a mixture bulk density of 1.0 g/cm$^3$, and cut to 1.2 cm×1.2 cm to prepare a negative electrode.

2. Method of Evaluation:

(Ionic conductivity): Measurement of ionic conductivity was conducted by an alternating current impedance method which comprises constructing an electrochemical cell by putting a polymer electrolyte between stainless steel electrodes at 25° C., passing an alternating current between the electrodes and measuring the resistant components, and the ionic conductivity was calculated from real-number impedance intercept in a Cole—Cole plot.

(Charging and discharging conditions of battery): Charging and discharging were carried out at 25° C. and at a current density of 0.5 mA/cm$^2$ using a charging and discharging device (TOSCAT 3000 manufactured by Toyo System Co., Ltd.). A constant current charging was carried out up to 4.2 V, and after the voltage reached 4.2 V, a constant voltage charging was carried out for 12 hours. Furthermore, a constant current discharging was carried out until a cut-off voltage of discharge reached 3.5 V. The capacity obtained by the first discharging was taken as an initial discharge capacity. Charging-discharging under the above conditions was 1 cycle, and the charging and the discharging were repeated until the capacity reached 70% or lower of the initial discharge capacity, and the number of repetition was taken as cycle characteristic. Furthermore, a constant current charging was carried out at a current density of 1 mA/cm$^2$ up to 4.2 V, and after the voltage reached 4.2 V, a constant voltage charging was carried out for 12 hours. Furthermore, a constant current discharging was carried out until a cut-off voltage of discharge reached 3.5 V. The resulting capacity and the initial cycle capacity obtained by the above charge and discharge cycle were compared, and the ratio was taken as a high-rate charge and discharge characteristics.

EXAMPLE 1

To a mixture of 230 g (1.0 mol) of dibutylene glycol monomethacrylate and 496 g (2.0 mols) of tributylene glycol monomethyl ether was added 207.6 g (2.0 mols) of trimethyl borate. The resulting mixture was maintained at 60° C. with stirring for 1 hour under a dry air atmosphere and then heated to 75° C. After the temperature reached 75° C., the pressure in the system was gradually reduced. While the pressure was maintained at 2.67 kPa (20 mmHg) or less for 6 hours, the volatile matters produced with the progress of boric acid transesterifications and the excess trimethyl borate were removed. Then, the residue was filtered to obtain 720 g of a polymerizable boron-containing compound A represented by (formula 1). An infrared absorption spectrum of the polymerizable boron-containing compound A obtained was measured to confirm the disappearance of an absorption band due to a hydroxyl group at 3,300 cm$^{-1}$.

Subsequently, 7.34 g (10 mmol) of the polymerizable boron-containing compound A, 7.34 mg of 2,2'-azobisisobutyronitrile and LiBF$_4$ as electrolytic salt were mixed. The resulting solution was poured into a polytetrafluoroethylene die and maintained at 80° C. for 6 hours to obtain a polyelectrolyte.

Out of the thus obtained electrolyte membrane, a circular membrane with a diameter of 1 cm was cut, and then held between a pair of stainless-steel electrodes, after which its ionic conductivity was determined at 25° C. by adopting the above-mentioned ionic conductivity measuring method. The ionic conductivity was 1.1 mS/cm, namely, a higher ionic conductivity could be attained as compared with Comparative Examples 1 and 2 described hereinafter.

Furthermore, the solution was cast on the positive electrode and negative electrode produced by the above-mentioned method, and kept at 80° C. for 6 hours to produce polymer electrolytes on the positive electrode and the negative electrode. Furthermore, these positive electrode and negative electrode were put one upon another, and these were stuck together by keeping them at 80° C. for 6 hours under application of a load of 0.1 MPa.

Figure 1:
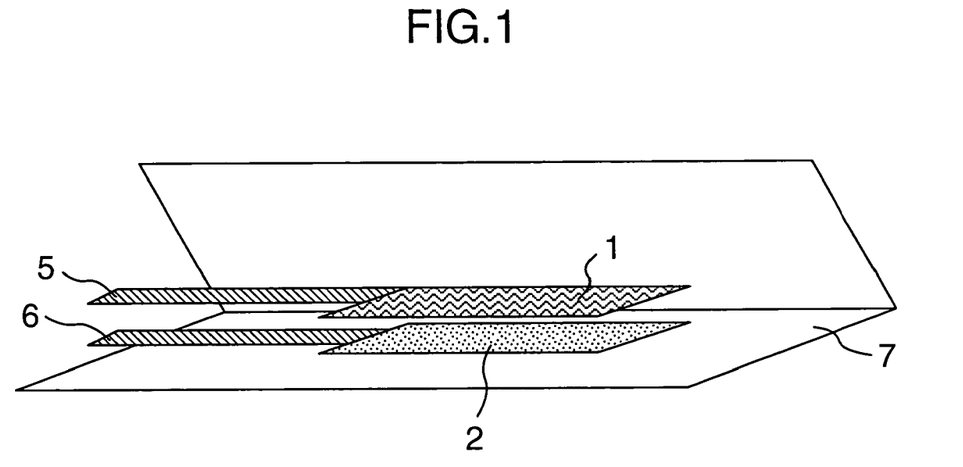
FIG. 1 is a schematic oblique view illustrating the structure of a test battery used in the examples.

Then, as shown in FIG. 1, stainless steel terminals 5 and 6 were attached to positive electrode 1 and negative electrode 2, and these were inserted in a bag-shaped aluminum laminate film 7. The initial discharge capacity of the obtained battery was 1.0 mAh, and the cycle characteristic was 138 times. Furthermore, the high rate discharge characteristic was 80%, and the battery was superior to those obtained in Comparative Examples 1 and 2 in initial discharge capacity, cycle characteristics and high rate discharge characteristics. When the aluminum laminate film of the battery was stripped off, there was recognized no flow of the electrolyte in the battery.

EXAMPLE 2

A polyelectrolyte and battery were obtained in exactly the same manner as in Example 1 except for using $LiPF_6$ as electrolytic salt in place of $LiBF_4$. Its ionic conductivity was determined by adopting the same measuring method as in Example 1. The ionic conductivity was 1.2 mS/cm, namely, a higher ionic conductivity could be attained as compared with Comparative Examples 1 and 2 described hereinafter.

The initial discharge capacity of the battery was 1.0 mAh, and the cycle characteristic was 138 times. Furthermore, high rate discharge characteristic was 80%, and the battery was superior to those obtained in Comparative Examples 1 and 2 in initial discharge capacity, cycle characteristics and high rate discharge characteristics. When the aluminum laminate film of the battery was stripped off, there was recognized no flow of the electrolyte in the battery.

EXAMPLE 3

A polyelectrolyte and battery were obtained in exactly the same manner as in Example 1 except for using $LiN(CF_3SO_2)_2$ as electrolytic salt in place of $LiBF_4$. Its ionic conductivity was determined by adopting the same measuring method as in Example 1. The ionic conductivity was 1.4 mS/cm, namely, a higher ionic conductivity could be attained as compared with Comparative Examples 1 and 2 described hereinafter.

The initial discharge capacity of the battery was 1.0 mAh, and the cycle characteristic was 138 times. Furthermore, high rate discharge characteristic was 80%, and the battery was superior to those obtained in Comparative Examples 1 and 2 in initial discharge capacity, cycle characteristics and high rate discharge characteristics. When the aluminum laminate film of the battery was stripped off, there was recognized no flow of the electrolyte in the battery.

EXAMPLE 4

To a mixture of 202 g (1.0 mol) of dipropylene glycol monomethacrylate and 412 g (2.0 mols) of tripropylene glycol monomethyl ether was added 207.6 g (2.0 mols) of trimethyl borate. The resulting mixture was maintained at 60° C. with stirring for 1 hour under a dry air atmosphere and then heated to 75° C. After the temperature reached 75° C., the pressure in the system was gradually reduced. While the pressure was maintained at 2.67 kPa (20 mmHg) or less for 6 hours, the volatile matters produced with the progress of boric acid transesterifications and the excess trimethyl borate were removed.

Then, the residue was filtered to obtain 610 g of a polymerizable boron-containing compound B represented by (formula 1). An infrared absorption spectrum of the polymerizable boron-containing compound B obtained was measured to confirm the disappearance of an absorption band due to a hydroxyl group at 3,300 $cm^{-1}$. Subsequently, 6.22 g (10 mmol) of the polymerizable boron-containing compound B, 6.22 mg of 2,2'-azobisisobutyronitrile and $LiBF_4$ as electrolytic salt were mixed. The resulting solution was poured into a polytetrafluoroethylene die and maintained at 80° C. for 6 hours to obtain a polyelectrolyte.

Out of the thus obtained electrolyte membrane, a circular-membrane with a diameter of 1 cm was cut, and then held between a pair of stainless-steel electrodes, after which its ionic conductivity was determined at 25° C. by adopting the above-mentioned ionic conductivity measuring method. The ionic conductivity was 1.4 mS/cm, namely, a higher ionic conductivity could be attained as compared with Comparative Examples 1 and 2 described hereinafter.

Furthermore, the solution was cast on the positive electrode and the negative electrode produced by the above-mentioned method, and kept at 80° C. for 6 hours to produce polymer electrolytes on the positive electrode and the negative electrode. Furthermore, these positive electrode and negative electrode were put one upon another, and these were stuck together by keeping them at 80° C. for 6 hours under application of a load of 0.1 MPa.

Then, as shown in FIG. 1, stainless steel terminals 5 and 6 were attached to positive electrode 1 and negative electrode 2, and these were inserted in a bag-shaped aluminum laminate film 7. The initial discharge capacity of the obtained battery was 1.0 mAh, and the cycle characteristic was 140 times. Furthermore, the high rate discharge characteristic was 80%, and the battery was superior to those obtained in Comparative Examples 1 and 2 in initial discharge capacity, cycle characteristics and high rate discharge characteristics. When the aluminum laminate film of the battery was stripped off, there was recognized no flow of the electrolyte in the battery.

EXAMPLE 5

A polyelectrolyte and battery were obtained in exactly the same manner as in Example 4 except for using $LiPF_6$ as electrolytic salt in place of $LiBF_4$. Its ionic conductance was determined by adopting the same measuring method as in Example 4. The ionic conductivity was 1.4 mS/cm, namely, a higher ionic conductivity could be attained as compared with Comparative Examples 1 and 2 described hereinafter.

The initial discharge capacity of the battery was 1.0 mAh, and the cycle characteristic was 140 times. Furthermore, the high rate discharge characteristic was 85%, and the battery was superior to those obtained in Comparative Examples 1 and 2 in initial discharge capacity, cycle characteristics and high rate discharge characteristics. When the aluminum laminate film of the battery was stripped off, there was recognized no flow of the electrolyte in the battery.

EXAMPLE 6

A polyelectrolyte and battery were obtained in exactly the same manner as in Example 4 except for using $LiN(CF_3SO_2)_2$ as electrolytic salt in place of $LiBF_4$. Its ionic conductivity was determined by adopting the same measuring method as in Example 4. The ionic conductivity was 1.5 mS/cm, namely, a higher ionic conductivity could be attained as compared with Comparative Examples 1 and 2 described hereinafter.

The initial discharge capacity of the battery was 1.0 mAh, and the cycle characteristic was 140 times. Furthermore, the high rate discharge characteristic was 85%, and the battery was superior to those obtained in Comparative Examples 1 and 2 in initial discharge capacity, cycle characteristics and high rate discharge characteristics. When the aluminum laminate film of the battery was stripped off, there was recognized no flow of the electrolyte in the battery.

EXAMPLE 7

To a mixture of 174 g (1.0 mol) of diethylene glycol monomethacrylate and 328 g (2.0 mols) of triethylene glycol monomethyl ether was added 207.6 g (2.0 mols) of trimethyl borate. The resulting mixture was maintained at 60° C. with stirring for 1 hour under a dry air atmosphere and then heated to 75° C. After the temperature reached 75° C., the pressure in the system was gradually reduced. While the pressure was maintained at 2.67 kPa (20 mmHg) or less for 6 hours, the volatile matters produced with the progress of boric acid transesterifications and the excess trimethyl borate were removed.

Then, the residue was filtered to obtain 495 g of a polymerizable boron-containing compound C represented by (formula 1). An infrared absorption spectrum of the polymerizable boron-containing compound C obtained was measured to confirm the disappearance of an absorption band due to a hydroxyl group at 3,300 cm$^{-1}$. Subsequently, 5.10 g (10 mmol) of the polymerizable boron-containing compound C, 5.10 mg of 2,2'-azobisisobutyronitrile and LiBF$_4$ as electrolytic salt were mixed. The resulting solution was poured into a polytetrafluoroethylene die and maintained at 80° C. for 6 hours to obtain a polyelectrolyte.

Out of the thus obtained electrolyte membrane, a circular membrane with a diameter of 1 cm was cut, and then held between a pair of stainless-steel electrodes, after which its ionic conductivity was determined at 25° C. by adopting the above-mentioned ionic conductivity measuring method. The ionic conductivity was 1.6 mS/cm, namely, a higher ionic conductivity could be attained as compared with Comparative Examples 1 and 2 described hereinafter.

Furthermore, the solution was cast on the positive electrode and the negative electrode produced by the above-mentioned method, and kept at 80° C. for 6 hours to produce polymer electrolytes on the positive electrode and the negative electrode. Furthermore, these positive electrode and negative electrode were put one upon another, and these were stuck together-by keeping them at 80° C. for 6 hours under application of a load of 0.1 MPa.

Then, as shown in FIG. 1, stainless steel terminals 5 and 6 were attached to positive electrode 1 and negative electrode 2, and these were inserted in a bag-shaped aluminum laminate film 7. The initial discharge capacity of the obtained battery was 1.0 mAh, and the cycle characteristic was 150 times. Furthermore, the high rate discharge characteristic was 85%, and the battery was superior to those obtained in Comparative Examples 1 and 2 in initial discharge capacity, cycle characteristics and high rate discharge characteristics. When the aluminum laminate film of the battery was stripped off, there was recognized no flow of the electrolyte in the battery.

EXAMPLE 8

A polyelectrolyte and battery were obtained in exactly the same manner as in Example 7 except for using LiPF$_6$ as electrolytic salt in place of LiBF$_4$. Its ionic conductance was determined by adopting the same measuring method as in Example 7. The ionic conductivity was 1.8 mS/cm, namely, a higher ionic conductivity could be attained as compared with Comparative Examples 1 and 2 described hereinafter.

The initial discharge capacity of the battery was 1.0 mAh, and the cycle characteristic was 150 times. Furthermore, the high rate discharge characteristic was 85%, and the battery was superior to those obtained in Comparative Examples 1 and 2 in initial discharge capacity, cycle characteristics and high rate discharge characteristics. When the aluminum laminate film of the battery was stripped off, there was recognized no flow of the electrolyte in the battery.

EXAMPLE 9

A polyelectrolyte and battery were obtained in exactly the same manner as in Example 7 except for using LiN(CF$_3$SO$_2$)$_2$ as electrolytic salt in place of LiBF$_4$. Its ionic conductance was determined by adopting the same measuring method as in Example 7. The ionic conductivity was 2.0 mS/cm, namely, a higher ionic conductivity could be attained as compared with Comparative Examples 1 and 2 described hereinafter.

The initial discharge capacity of the battery was 1.0 mAh, and the cycle characteristic was 150 times. Furthermore, the high rate discharge characteristic was 85%, and the battery was superior to those obtained in Comparative Examples 1 and 2 in initial discharge capacity, cycle characteristics and high rate discharge characteristics. When the aluminum laminate film of the battery was stripped off, there was recognized no flow of the electrolyte in the battery.

EXAMPLE 10

To 690 g (3.0 mols) of dibutylene glycol monomethacrylate was added 207.6 g (2.0 mols) of trimethyl borate. The resulting mixture was heated to 60° C. with stirring under a dry air atmosphere. The mixture was maintained at 60° C. for 1 hour and then heated to 75° C. After the temperature reached 75° C., the pressure in the system was gradually reduced. While the pressure was maintained at 2.67 kPa (20 mmHg) or less for 6 hours, the volatile matter produced with the progress of boric acid transesterification and the excess trimethyl borate were removed.

Then, the residue was filtered to obtain 685 g of a polymerizable boron-containing compound (a boric acid esterification product of dibutylene glycol monomethacrylate) D represented by (formula 2). An infrared absorption spectrum of the polymerizable boron-containing compound D obtained was measured to confirm the disappearance of an absorption band due to a hydroxyl group at 3,300 cm$^{-1}$.

Next, 207.6 g (2.0 mols) of trimethyl borate was added to 744 g (3.0 mols) of tributylene glycol monomethyl ether. The resulting mixture was heated to 60° C. with stirring under a dry nitrogen atmosphere. The mixture was maintained at 60° C. for 1 hour and then heated to 120° C. over a period of 1 hour. After the temperature reached 120° C., the pressure in the system was gradually reduced. While the pressure was maintained at 2.67 kPa (20 mmHg) or less for 3 hours, the volatile matter produced with the progress of boric acid transesterification and the excess trimethyl borate were removed.

Then, the residue was filtered to obtain 740 g of a boron-containing compound (a boric acid esterification product of tributylene glycol monomethyl ether) E represented by (formula 3). An infrared absorption spectrum of the polymerizable boron-containing compound E obtained was measured to confirm the disappearance of an absorption band due to a hydroxyl group at 3,300 cm$^{-1}$.

Subsequently, 6.98 g (10 mmol) of the polymerizable boron-containing compound (the boric acid esterification product of dibutylene glycol monometh-acrylate) D, 7.52 g (10 mmol) of the boron-containing compound (the boric acid esterification product of tributylene glycol monomethyl ether) E, 6.98 mg of 2,2'-azobisisobutyronitrile and $LiBF_4$ as electrolytic salt were mixed. The resulting solution was poured into a polytetrafluoroethylene die and maintained at 80° C. for 6 hours to obtain a polyelectrolyte.

Out of the thus obtained electrolyte membrane, a circular membrane with a diameter of 1 cm was cut, and then held between a pair of stainless-steel electrodes, after which its ionic conductivity was determined at 25° C. by adopting the above-mentioned ionic conductivity measuring method. The ionic conductivity was 1.1 mS/cm, namely, a higher ionic conductivity could be attained as compared with Comparative Examples 1 and 2 described hereinafter.

Furthermore, the solution was cast on the positive electrode and the negative electrode produced by the above-mentioned method, and kept at 80° C. for 6 hours to produce polymer electrolytes on the positive electrode and the negative electrode. Furthermore, these positive electrode and negative electrode were put one upon another, and these were stuck together by keeping at 80° C. for 6 hours under application of a load of 0.1 MPa.

Then, as shown in FIG. 1, stainless steel terminals 5 and 6 were attached to positive electrode 1 and negative electrode 2, and these were inserted in a bag-shaped aluminum laminate film 7. The initial discharge capacity of the obtained battery was 1.1 mAh, and the cycle characteristic was 150 times. Furthermore, the high rate discharge characteristic was 88%, and the battery was superior to those obtained in Comparative Examples 1 and 2 in initial discharge capacity, cycle characteristics and high rate discharge characteristics. When the aluminum laminate film of the battery was stripped off, there was recognized no flow of the electrolyte in the battery.

EXAMPLE 11

A polyelectrolyte and battery were obtained in exactly the same manner as in Example 10 except for using $LiPF_6$ as electrolytic salt in place of $LiBF_4$. Its ionic conductance was determined by adopting the same measuring method as in Example 10. The ionic conductivity was 1.1 mS/cm, namely, a higher ionic conductivity could be attained as compared with Comparative Examples 1 and 2 described hereinafter.

The initial discharge capacity of the battery was 1.1 mAh, and the cycle characteristic was 175 times. Furthermore, the high rate discharge characteristic was 88%, and the battery was superior to those obtained in Comparative Examples 1 and 2 in initial discharge capacity, cycle characteristics and high rate discharge characteristics. When the aluminum laminate film of the battery was stripped off, there was recognized no flow of the electrolyte in the battery.

EXAMPLE 12

A polyelectrolyte and battery were obtained in exactly the same manner as in Example 10 except for using $LiN(CF_3SO_2)_2$ as electrolytic salt in place of $LiBF_4$. Its ionic conductivity was determined by adopting the same measuring method as in Example 10. The ionic conductivity was 1.1 mS/cm, namely, a higher ionic conductivity could be attained as compared with Comparative Examples 1 and 2 described hereinafter.

The initial discharge capacity of the battery was 1.1 mAh, and the cycle characteristic was 175 times. Furthermore, the high rate discharge characteristic was 88%, and the battery was superior to those obtained in Comparative Examples 1 and 2 in initial discharge capacity, cycle characteristics and high rate discharge characteristics. When the aluminum laminate film of the battery was stripped off, there was recognized no flow of the electrolyte in the battery.

EXAMPLE 13

To 606 g (3.0 mols) of dipropylene glycol monomethacrylate was added 207.6 g (2.0 mols) of trimethyl borate. The resulting mixture was heated to 60° C. with stirring under a dry air atmosphere. The mixture was maintained at 60° C. for 1 hour and then heated to 75° C. After the temperature reached 75° C., the pressure in the system was gradually reduced. While the pressure was maintained at 2.67 kPa (20 mmHg) or less for 6 hours, the volatile matter produced with the progress of boric acid transesterification and the excess trimethyl borate were removed.

Then, the residue was filtered to obtain 600 g of a polymerizable boron-containing compound (a boric acid esterification product of dipropylene glycol monomethacrylate) F represented by (formula 2). An infrared absorption spectrum of the polymerizable boron-containing compound F obtained was measured to confirm the disappearance of an absorption band due to a hydroxyl group at 3,300 $cm^{-1}$.

Next, 207.6 g (2.0 mols) of trimethyl borate was added to 618 g (3.0 mols) of tripropylene glycol monomethyl ether. The resulting mixture was heated to 60° C. with stirring under a dry nitrogen atmosphere. The mixture was maintained at 60° C. for 1 hour and then heated to 120° C. over a period of 1 hour. After the temperature reached 120° C., the pressure in the system was gradually reduced. While the pressure was maintained at 2.67 kPa (20 mmHg) or less for 3 hours, the volatile matter produced with the progress of boric acid transesterification and the excess trimethyl borate were removed. Then, the residue was filtered to obtain 610 g of a boron-containing compound (a boric acid esterification product of tripropylene glycol monomethyl ether) G represented by (formula 3). An infrared absorption spectrum of the polymerizable boron-containing compound G obtained was measured to confirm the disappearance of an absorption band due to a hydroxyl group at 3,300 $cm^{-1}$.

Subsequently, 6.14 g (10 mmol) of the polymerizable boron-containing compound (the boric acid esterification product of dipropylene glycol monomethacrylate) F, 6.26 g (10 mmol) of the boron-containing compound (the boric acid esterification product of tripropylene glycol monomethyl ether) G, 6.14 mg of 2,2'-azobisisobutyronitrile and $LiBF_4$ as electrolytic salt were mixed.

The resulting solution was poured into a polytetrafluoroethylene die and maintained at 80° C. for 6 hours to obtain a polyelectrolyte. Out of the thus obtained electrolyte membrane, a circular membrane with a diameter of 1 cm was cut, and then held between a pair of stainless-steel electrodes, after which its ionic conductivity was determined at 25° C. by adopting the above-mentioned ionic conductivity measuring method. The ionic conductivity was 1.2 mS/cm, namely, a higher ionic conductivity could be attained as compared with Comparative Examples 1 and 2 described hereinafter.

Furthermore, the solution was cast on the positive electrode and the negative electrode produced by the above-mentioned method, and kept at 80° C. for 6 hours to produce polymer electrolytes on the positive electrode and the negative electrode. Furthermore, these positive electrode and negative electrode were put one upon another, and these were stuck together by keeping at 80° C. for 6 hours under application of a load of 0.1 MPa.

Then, as shown in FIG. 1, stainless steel terminals 5 and 6 were attached to positive electrode 1 and negative electrode 2, and these were inserted in a bag-shaped aluminum laminate film 7. The initial discharge capacity of the obtained battery was 1.2 mAh, and the cycle characteristic was 175 times. Furthermore, the high rate discharge characteristic was 88%, and the battery was superior to those obtained in Comparative Examples 1 and 2 in initial discharge capacity, cycle characteristics and high rate discharge characteristics. When the aluminum laminate film of the battery was stripped off, there was recognized no flow of the electrolyte in the battery.

EXAMPLE 14

A polyelectrolyte and battery were obtained in exactly the same manner as in Example 13 except for using $LiPF_6$ as electrolytic salt in place of $LiBF_4$. Its ionic conductance was determined by adopting the same measuring method as in Example 13. The ionic conductivity was 1.2 mS/cm, namely, a higher ionic conductivity could be attained as compared with Comparative Examples 1 and 2 described hereinafter.

The initial discharge capacity of the battery was 1.2 mAh, and the cycle characteristic was 188 times. Furthermore, the high rate discharge characteristic was 90%, and the battery was superior to those obtained in Comparative Examples 1 and 2 in initial discharge capacity, cycle characteristics and high rate discharge characteristics. When the aluminum laminate film of the battery was stripped off, there was recognized no flow of the electrolyte in the battery.

EXAMPLE 15

A polyelectrolyte and battery were obtained in exactly the same manner as in Example 13 except for using LiN$(CF_3SO_2)_2$ as electrolytic salt in place of $LiBF_4$. Its ionic conductivity was determined by adopting the same measuring method as in Example 13. The ionic conductivity was 1.2 mS/cm, namely, a higher ionic conductivity could be attained as compared with Comparative Examples 1 and 2 described hereinafter.

The initial discharge capacity of the battery was 1.2 mAh, and the cycle characteristic was 188 times. Furthermore, the high rate discharge characteristic was 90%, and the battery was superior to those obtained in Comparative Examples 1 and 2 in initial discharge capacity, cycle characteristics and high rate discharge characteristics. When the aluminum laminate film of the battery was stripped off, there was recognized no flow of the electrolyte in the battery.

EXAMPLE 16

To 522 g (3.0 mols) of diethylene glycol monomethacrylate was added 207.6 g (2.0 mols) of trimethyl borate. The resulting mixture was heated to 60° C. with stirring under a dry air atmosphere. The mixture was maintained at 60° C. for 1 hour and then heated to 75° C. After the temperature reached 75° C., the pressure in the system was gradually reduced. While the pressure was maintained at 2.67 kPa (20 mmHg) or less for 6 hours, the volatile matter produced with the progress of boric acid transesterification and the excess trimethyl borate were removed. Then, the residue was filtered to obtain 515 g of a polymerizable boron-containing compound (a boric acid esterification product of diethylene glycol monomethacrylate) H represented by (formula 2). An infrared absorption spectrum of the polymerizable boron-containing compound H obtained was measured to confirm the disappearance of an absorption band due to a hydroxyl group at 3,300 $cm^{-1}$.

Next, 207.6 g (2.0 mols) of trimethyl borate was added to 492 g (3.0 mols) of triethylene glycol monomethyl ether. The resulting mixture was heated to 60° C. with stirring under a dry nitrogen atmosphere. The mixture was maintained at 60° C. for 1 hour and then heated to 120° C. over a period of 1 hour. After the temperature reached 120° C., the pressure in the system was gradually reduced. While the pressure was maintained at 2.67 kPa (20 mmHg) or less for 3 hours, the volatile matter produced with the progress of boric acid transesterification and the excess trimethyl borate were removed.

Then, the residue was filtered to obtain 485 g of a boron-containing compound (a boric acid esterification product of triethylene glycol monomethyl ether) I represented by (formula 3). An infrared absorption spectrum of the polymerizable boron-containing compound I obtained was measured to confirm the disappearance of an absorption band due to a hydroxyl group at 3,300 $cm^{-1}$.

Subsequently, 5.30 g (10 mmol) of the polymerizable boron-containing compound (the boric acid esterification product of diethylene glycol monomethacrylate) H, 5.00 g (10 mmol) of the boron-containing compound (the boric acid esterification product of triethylene glycol monomethyl ether) I, 5.30 mg of 2,2'-azobisisobutyronitrile and $LiBF_4$ as electrolytic salt were mixed. The resulting solution was poured into a polytetrafluoroethylene die and maintained at 80° C. for 6 hours to obtain a polyelectrolyte.

Out of the thus obtained electrolyte membrane, a circular membrane with a diameter of 1 cm was cut, and then held between a pair of stainless-steel electrodes, after which its ionic conductivity was determined at 25° C. by adopting the above-mentioned ionic conductivity measuring method. The ionic conductivity was 1.3 mS/cm, namely, a higher ionic conductivity could be attained as compared with Comparative Examples 1 and 2 described hereinafter.

Furthermore, the solution was cast on the positive electrode and the negative electrode produced by the above-mentioned method, and kept at 80° C. for 6 hours to produce polymer electrolytes on the positive electrode and the negative electrode. Furthermore, these positive electrode and negative electrode were put one upon another, and these were stuck together by keeping them at 80° C. for 6 hours under application of a load of 0.1 MPa.

Then, as shown in FIG. 1, stainless steel terminals 5 and 6 were attached to positive electrode 1 and negative electrode 2, and these were inserted in a bag-shaped aluminum laminate film 7. The initial discharge capacity of the obtained battery was 1.3 mAh, and the cycle characteristic was 188 times. Furthermore, the high rate discharge characteristic was 90%, and the battery was superior to those obtained in Comparative Examples 1 and 2 in initial discharge capacity, cycle characteristics and high rate discharge characteristics. When the aluminum laminate film of the battery was stripped off, there was recognized no flow of the electrolyte in the battery.

EXAMPLE 17

A polyelectrolyte and battery were obtained in exactly the same manner as in Example 16 except for using $LiPF_6$ as electrolytic salt in place of $LiBF_4$. Its ionic conductance was determined by adopting the same measuring method as in Example 16. The ionic conductivity was 1.3 mS/cm, namely, a higher ionic conductivity could be attained as compared with Comparative Examples 1 and 2 described hereinafter.

The initial discharge capacity of the battery was 1.3 mAh, and the cycle characteristic was 190 times. Furthermore, the high rate discharge characteristic was 92%, and thus the battery was superior to those obtained in Comparative Examples 1 and 2 in initial discharge capacity, cycle characteristics and high rate discharge characteristics. When the aluminum laminate film of the battery was stripped off, there was recognized no flow of the electrolyte in the battery.

EXAMPLE 18

A polyelectrolyte and battery were obtained in exactly the same manner as in Example 16 except for using LiN$(CF_3SO_2)_2$ as electrolytic salt in place of LiBF$_4$. Its ionic conductivity was determined by adopting the same measuring method as in Example 16. The ionic conductivity was 1.3 mS/cm, namely, a higher ionic conductivity could be attained as compared with Comparative Examples 1 and 2 described hereinafter.

The initial discharge capacity of the battery was 1.3 mAh, and the cycle characteristic was 190 times. Furthermore, the high rate discharge characteristic was 92%, and thus the battery was superior to those obtained in Comparative Examples 1 and 2 in initial discharge capacity, cycle characteristics and high rate discharge characteristics. When the aluminum laminate film of the battery was stripped off, there was recognized no flow of the electrolyte in the battery.

EXAMPLE 19

A polyelectrolyte and battery were obtained in exactly the same manner as in Example 10 except for changing the amount of the boron-containing compound (the boric acid esterification product of tributylene glycol monomethyl ether) E blended from 7.52 g (10 mmol) to 15.0 g (20 mmol).

Out of the thus obtained electrolyte membrane, a circular membrane with a diameter of 1 cm was cut, and then held between a pair of stainless-steel electrodes, after which its ionic conductivity was determined at 25° C. by adopting the above-mentioned ionic conductivity measuring method. The ionic conductivity was 1.4 mS/cm, namely, a higher ionic conductivity could be attained as compared with Comparative Examples 1 and 2 described hereinafter.

The initial discharge capacity of the battery was 1.4 mAh, and the cycle characteristic was 210 times. Furthermore, the high rate discharge characteristic was 92%, and thus the battery was superior to those obtained in Comparative Examples 1 and 2 in initial discharge capacity, cycle characteristics and high rate discharge characteristics. When the aluminum laminate film of the battery was stripped off, there was recognized no flow of the electrolyte in the battery.

EXAMPLE 20

A polyelectrolyte and battery were obtained in exactly the same manner as in Example 19 except for using LiPF$_6$ as electrolytic salt in place of LiBF$_4$. Its ionic conductance was determined by adopting the same measuring method as in Example 19. The ionic conductivity was 1.4 mS/cm, namely, a higher ionic conductivity could be attained as compared with Comparative Examples 1 and 2 described hereinafter.

The initial discharge capacity of the battery was 1.4 mAh, and the cycle characteristic was 210 times. Furthermore, the high rate discharge characteristic was 92%, and thus the battery was superior to those obtained in Comparative Examples 1 and 2 in initial discharge capacity, cycle characteristics and high rate discharge characteristics. When the aluminum laminate film of the battery was stripped off, there was recognized no flow of the electrolyte in the battery.

EXAMPLE 21

A polyelectrolyte and battery were obtained in exactly the same manner as in Example 19 except for using LiN$(CF_3SO_2)_2$ as electrolytic salt in place of LiBF$_4$. Its ionic conductivity was determined by adopting the same measuring method as in Example 19. The ionic conductivity was 1.6 mS/cm, namely, a higher ionic conductivity could be attained as compared with Comparative Examples 1 and 2 described hereinafter.

The initial discharge capacity of the battery was 1.6 mAh, and the cycle characteristic was 215 times. Furthermore, the high rate discharge characteristic was 95%, and thus the battery was superior to those obtained in Comparative Examples 1 and 2 in initial discharge capacity, cycle characteristics and high rate discharge characteristics. When the aluminum laminate film of the battery was stripped off, there was recognized no flow of the electrolyte in the battery.

EXAMPLE 22

A polyelectrolyte and battery were obtained in exactly the same manner as in Example 13 except for changing the amount of the boron-containing compound (the boric acid esterification product of tripropylene glycol monomethyl ether) G blended from 6.26 g (10 mmol) to 12.5 g (20 mmol).

The ionic conductivity was 1.6 mS/cm, namely, a higher ionic conductivity could be attained as compared with Comparative Examples 1 and 2 described hereinafter.

The initial discharge capacity of the battery was 1.6 mAh, and the cycle characteristic was 215 times. Furthermore, the high rate discharge characteristic was 95%, and thus the battery was superior to those obtained in Comparative Examples 1 and 2 in initial discharge capacity, cycle characteristics and high rate discharge characteristics. When the aluminum laminate film of the battery was stripped off, there was recognized no flow of the electrolyte in the battery.

EXAMPLE 23

A polyelectrolyte and battery were obtained in exactly the same manner as in Example 22 except for using LiPF$_6$ as electrolytic salt in place of LiBF$_4$. Its ionic conductance was determined by adopting the same measuring method as in Example 22. The ionic conductivity was 1.6 mS/cm, namely, a higher ionic conductivity could be attained as compared with Comparative Examples 1 and 2 described hereinafter.

The initial discharge capacity of the battery was 1.6 mAh, and the cycle characteristic was 225 times. Furthermore, the high rate discharge characteristic was 95%, and thus the battery was superior to those obtained in Comparative Examples 1 and 2 in initial discharge capacity, cycle characteristics and high rate discharge characteristics. When the aluminum laminate film of the battery was stripped off, there was recognized no flow of the electrolyte in the battery.

EXAMPLE 24

A polyelectrolyte and battery were obtained in exactly the same manner as in Example 22 except for using LiN(CF$_3$SO$_2$)$_2$ as electrolytic salt in place of LiBF$_4$. Its ionic conductivity was determined by adopting the same measuring method as in Example 22. The ionic conductivity was 1.8 mS/cm, namely, a higher ionic conductivity could be attained as compared with Comparative Examples 1 and 2 described hereinafter.

The initial discharge capacity of the battery was 1.8 mAh, and the cycle characteristic was 225 times. Furthermore, the high rate discharge characteristic was 95%, and thus the battery was superior to those obtained in Comparative Examples 1 and 2 in initial discharge capacity, cycle characteristics and high rate discharge characteristics. When the aluminum laminate film of the battery was stripped off, there was recognized no flow of the electrolyte in the battery.

EXAMPLE 25

A polyelectrolyte and battery were obtained in exactly the same manner as in Example 16 except for changing the amount of the boron-containing compound (the boric acid esterification product of triethylene glycol monomethyl ether) I blended from 5.00 g (10 mmol) to 10.0 g (20 mmol).

The ionic conductivity was 1.8 mS/cm, namely, a higher ionic conductivity could be attained as compared with Comparative Examples 1 and 2 described hereinafter.

The initial discharge capacity of the battery was 1.8 mAh, and the cycle characteristic was 240 times. Furthermore, the high rate discharge characteristic was 95%, and thus the battery was superior to those obtained in Comparative Examples 1 and 2 in initial discharge capacity, cycle characteristics and high rate discharge characteristics. When the aluminum laminate film of the battery was stripped off, there was recognized no flow of the electrolyte in the battery.

EXAMPLE 26

A polyelectrolyte and battery were obtained in exactly the same manner as in Example 25 except for using LiPF$_6$ as electrolytic salt in place of LiBF$_4$. Its ionic conductance was determined by adopting the same measuring method as in Example 25. The ionic conductivity was 1.8 mS/cm, namely, a higher ionic conductivity could be attained as compared with Comparative Examples 1 and 2 described hereinafter.

The initial discharge capacity of the battery was 1.8 mAh, and the cycle characteristic was 240 times. Furthermore, the high rate discharge characteristic was 95%, and thus the battery was superior to those obtained in Comparative Examples 1 and 2 in initial discharge capacity, cycle characteristics and high rate discharge characteristics. When the aluminum laminate film of the battery was stripped off, there was recognized no flow of the electrolyte in the battery.

EXAMPLE 27

A polyelectrolyte and battery were obtained in exactly the same manner as in Example 25 except for using LiN(CF$_3$SO$_2$)$_2$ as electrolytic salt in place of LiBF$_4$. Its ionic conductivity was determined by adopting the same measuring method as in Example 25. The ionic conductivity was 2.0 mS/cm, namely, a higher ionic conductivity could be attained as compared with Comparative Examples 1 and 2 described hereinafter.

The initial discharge capacity of the battery was 1.8 mAh, and the cycle characteristic was 250 times. Furthermore, the high rate discharge characteristic was 95%, and thus the battery was superior to those obtained in Comparative Examples 1 and 2 in initial discharge capacity, cycle characteristics and high rate discharge characteristics. When the aluminum laminate film of the battery was stripped off, there was recognized no flow of the electrolyte in the battery.

EXAMPLE 28

A polymer electrolyte and a battery were produced in the same manner as in Example 16, except that the amount of the polymerizable boron-containing compound H (an esterification product of boric acid with diethylene glycol monomethacrylate) was 1.59 g (10 mmol) instead of 5.30 g (3 mmol), and the amount of the polymerizable boron-containing compound I (an esterification product of boric acid with triethylene glycol monomethyl ether) was 8.5 g (17 mmol) instead of 5.00 g (10 mmol). The ionic conductivity of the polymer electrolyte was 2.1 mS/cm, which was higher than that obtained in Comparative Examples 1 and 2 given hereinafter.

The initial discharge capacity of the battery was 1.9 mAh, and the cycle characteristic was 255 times. Furthermore, the high rate discharge characteristic was 96%, and thus the battery was superior to those obtained in Comparative Examples 1 and 2 in initial discharge capacity, cycle characteristics and high rate discharge characteristics. When the aluminum laminate film of the battery was stripped off, there was recognized no flow of the electrolyte in the battery.

EXAMPLE 29

A polymer electrolyte and a battery were produced in the same manner as in Example 28, except that LiPF$_6$ was used in place of LiBF$_4$ as the electrolytic salt. The ionic conductivity of the polymer electrolyte was 2.1 mS/cm, which was higher than that obtained in Comparative Examples 1 and 2 given hereinafter.

The initial discharge capacity of the battery was 1.9 mAh, and the cycle characteristic was 255 times. Furthermore, the high rate discharge characteristic was 96%, and thus the battery was superior to those obtained in Comparative Examples 1 and 2 in initial discharge capacity, cycle characteristics and high rate discharge characteristics. When the aluminum laminate film of the battery was stripped off, there was recognized no flow of the electrolyte in the battery.

EXAMPLE 30

A polymer electrolyte and a battery were produced in the same manner as in Example 28, except that LiN(CF$_3$SO$_2$)$_2$ was used in place of LiBF$_4$ as the electrolytic salt. The ionic conductivity of the polymer electrolyte was 2.0 mS/cm, which was higher than that obtained in Comparative Examples 1 and 2 given hereinafter.

The initial discharge capacity of the battery was 1.3 mAh, and the cycle characteristic was 260 times. Furthermore, the high rate discharge characteristic was 96%, and thus the battery was superior to those obtained in Comparative Examples 1 and 2 in initial discharge capacity, cycle characteristics and high rate discharge characteristics. When the aluminum laminate film of the battery was stripped off, there was recognized no flow of the electrolyte in the battery.

COMPARATIVE EXAMPLE 1

To 1,308 g (3.0 mols) of BLEMMER PE-350 (polyethylene glycol(350) monomethacrylate, mfd. by NOF CORPORATION) as starting material was added 34.8 g (0.5 mol) of boric anhydride. The resulting mixture was heated to 70° C. under a dry air atmosphere. After the temperature reached 70° C., the pressure in the system was gradually reduced. While the pressure was maintained at 2.67 kPa (20 mmHg) or less for 15 hours, water produced with the progress of the reaction was removed.

Then, the residue was filtered to obtain a polymerizable boron-containing compound J. Thereafter, 2.58 g of LiN(CF$_3$SO$_2$)$_2$ was uniformly dissolved as electrolytic salt in 4.00 g of the polymerizable boron-containing compound J, and the resulting solution was poured into a polytetrafluoroethylene die and maintained at 80° C. for 6 hours to obtain a polyelectrolyte, and then using this solution the ionic conductivity of the polymer electrolyte was measured by the same method as in Example 1. The ionic conductivity obtained was 0.025 mS/cm. Furthermore, the solution was cast on the positive electrode and the negative electrode produced by the above-mentioned method, and kept at 80° C. for 6 hours to produce polymer electrolytes on the positive electrode and the negative electrode. Furthermore, these positive electrode and negative electrode were put one upon another, and these were stuck together by keeping them at 80° C. for 6 hours under application of a load of 0.1 MPa.

Then, as shown in FIG. 1, stainless steel terminals 5 and 6 were attached to positive electrode 1 and negative electrode 2, and these were inserted in a bag-shaped aluminum laminate film 7. The initial discharge capacity of the obtained battery was 0.00009 mAh, and the cycle characteristic was 3 times. Furthermore, the high rate discharge characteristic was 5%. When the aluminum laminate film of the battery was stripped off, there was recognized no flow of the electrolyte in the battery.

COMPARATIVE EXAMPLE 2

To 550 g (1.0 mol) of methoxypolyethylene glycol with a molecular weight of 550 as starting material was added 11.6 g (0.167 mol) of boric anhydride. The resulting mixture was heated to 110° C. under a nitrogen gas atmosphere. After the temperature reached 110° C., the pressure in the system was gradually reduced. While the pressure was maintained at 2.67 kPa (20 mmHg) or less for 3 hours, water produced with the progress of the reaction was removed.

Then, the residue was filtered to obtain a boron-containing compound K. Thereafter, 2.00 g of the polymerizable boron-containing compound J was mixed with 2.00 g of the boron-containing compound K, followed by adding thereto 2.81 g of LiN(CF$_3$SO$_2$)$_2$ as electrolytic salt. After they were subjected to uniform dissolution, the ionic conductivity off the solution was measured in the same manner as in Example 1. The ionic conductivity was 0.020 mS/cm.

Furthermore, the solution was cast on the positive electrode and the negative electrode produced by the above-mentioned method, and kept at 80° C. for 6 hours to produce polymer electrolytes on the positive electrode and the negative electrode. Furthermore, these positive electrode and negative electrode were put one upon another, and these were stuck together by keeping them at 80° C. for 6 hours under application of a load of 0.1 MPa.

Then, as shown in FIG. 1, stainless steel terminals 5 and 6 were attached to positive electrode 1 and negative electrode 2, and these were inserted in a bag-shaped aluminum laminate film 7. The initial discharge capacity of the obtained battery was 0.0009 mAh, and the cycle characteristic was 10 times. Furthermore, the high rate discharge characteristic was 10%. When the aluminum laminate film of the battery was stripped off, there was recognized no flow of the electrolyte in the battery.

Table 2 shows the results of evaluation obtained for the examples and comparative examples described above.

TABLE 2

| Example | Ionic conductivity (mS/cm) | Initial discharge capacity (mAh) | Cycle performance (cycle number) | High-rate discharge characteristics (%) |
|---|---|---|---|---|
| 1 | 1.1 | 1 | 138 | 80 |
| 2 | 1.2 | 1 | 138 | 80 |
| 3 | 1.4 | 1 | 138 | 80 |
| 4 | 1.4 | 1 | 140 | 80 |
| 5 | 1.4 | 1 | 140 | 85 |
| 6 | 1.5 | 1 | 140 | 85 |
| 7 | 1.6 | 1 | 150 | 85 |
| 8 | 1.8 | 1 | 150 | 85 |
| 9 | 2.0 | 1 | 150 | 85 |
| 10 | 1.1 | 1.1 | 150 | 88 |
| 11 | 1.1 | 1.1 | 175 | 88 |
| 12 | 1.1 | 1.1 | 175 | 88 |
| 13 | 1.2 | 1.2 | 175 | 88 |
| 14 | 1.2 | 1.2 | 188 | 90 |
| 15 | 1.2 | 1.2 | 188 | 90 |
| 16 | 1.3 | 1.3 | 188 | 90 |
| 17 | 1.3 | 1.3 | 190 | 92 |
| 18 | 1.3 | 1.3 | 200 | 92 |
| 19 | 1.4 | 1.4 | 210 | 92 |
| 20 | 1.4 | 1.4 | 210 | 92 |
| 21 | 1.6 | 1.6 | 215 | 95 |
| 22 | 1.6 | 1.6 | 215 | 95 |
| 23 | 1.6 | 1.6 | 225 | 95 |
| 24 | 1.8 | 1.8 | 225 | 95 |
| 25 | 1.8 | 1.8 | 240 | 95 |
| 26 | 1.8 | 1.8 | 240 | 95 |
| 27 | 2.0 | 1.8 | 250 | 95 |
| 28 | 2.1 | 1.9 | 255 | 96 |
| 29 | 2.1 | 1.9 | 255 | 96 |
| 30 | 2.2 | 1.3 | 260 | 96 |
| Comparative Example 1 | 0.025 | 0.00009 | 3 | 5 |
| Comparative Example 2 | 0.020 | 0.0009 | 10 | 10 |

According to the present invention, a highly ion-conductive polyelectrolyte can be obtained.

It should be further understood by those skilled in the art that although the foregoing description has been made on embodiments of the invention, the invention is not limited thereto and various changes and modifications may be made without departing from the spirit of the invention and the scope of the appended claims.

What is claimed is:

1. A polymerizable composition for electrochemical device comprising a boron-containing compound represented by (formula 2) and a boron-containing compound represented by (formula 3) so that the molar ratio between the compound of (formula 2) and the compound of (formula 3) [(the number of moles of the compound of (formula 3))/(the number of moles of the compound of (formula 2))] is 0.1 to 9:

(Formula 2)

(Formula 3)

wherein B is a boron atom; $Z_4$, $Z_5$ and $Z_6$ are independently an organic group having an acryloyl or methacryloyl group, or a hydrocarbon group of 1 to 10 carbon atoms, provided that at least one of $Z_4$, $Z_5$ and $Z_6$ is an organic group having an acryloyl or methacryloyl group; $R_1$, $R_2$ and $R_3$ are independently a hydrocarbon group of 1 to 10 carbon atoms; AOs are independently an oxyalkylene group of 1 to 6 carbon atoms and are of one or more kinds; and p, q, r, $\alpha$, $\beta$ and $\gamma$ are independently an average number of moles of the oxyalkylene group(s) added of less than 4 and more than 0, provided that each of the sum p+q+r and the sum $\alpha+\beta+\gamma$ is 1 or more.

2. A polymerizable composition for electrochemical device comprising a boron-containing compound represented by (formula 2) and a boron-containing compound represented by (formula 3) so that the molar ratio between the compound of (formula 2) and the compound of (formula 3) [(the number of moles of the compound of (formula 3))/(the number of moles of the compound of (formula 2))] is 0.1 to 4:

(Formula 2)

(Formula 3)

wherein B is a boron atom; $Z_4$, $Z_5$ and $Z_6$ are independently an organic group having an acryloyl or methacryloyl group, or a hydrocarbon group of 1 to 10 carbon atoms, provided that at least one of $Z_4$, $Z_5$ and $Z_6$ is an organic group having an acryloyl or methacryloyl group; $R_1$, $R_2$ and $R_3$ are independently a hydrocarbon group of 1 to 10 carbon atoms; AOs are independently an oxyalkylene group of 1 to 6 carbon atoms and are of one or more kinds; and p, q, r, $\alpha$, $\beta$ and $\gamma$ are independently an average number of moles of the oxyalkylene group(s) added of less than 4 and more than 0, provided that each of the sum p+q+r and the sum $\alpha+\beta+\gamma$ is 1 or more.

3. An ion-conductive polyelectrolyte for electrochemical device comprising a polymer obtained by polymerizing a polymerizable composition according to claim 1.

4. An ion-conductive polyelectrolyte for electrochemical device comprising a polymer obtained by polymerizing a polymerizable composition according to claim 2.

5. An ion-conductive polyelectrolyte for electrochemical device comprising a polymer obtained by polymerizing a polymerizable composition according to claim 1 and at least one electrolytic salt.

6. An ion-conductive polyelectrolyte for electrochemical device comprising a polymer obtained by polymerizing a polymerizable composition according to claim 2 and at least one electrolytic salt.

7. An ion-conductive polyelectrolyte for electrochemical device according to claim 4, wherein said electrolytic salt is selected from the group consisting of $LiPF_6$, $LiN(CF_3SO_2)_2$, $LiClO_4$, $LiBF_4$, $LiAsF_6$, LiI, LiBr, LiSCN, $Li_2B_{10}Cl_{10}$ and $LiCF_3CO_2$.

8. The polymerizable composition according to claim 1, wherein the oxyalkylene groups have 2 to 4 carbon atoms.

9. The polymerizable composition according to claim 1, wherein said molar ratio between the compound of (formula 2) and the compound of (formula 3) is 0.5 to 4.

10. The ion-conductive polyelectrolyte for electrochemical device according to claim 5, wherein a molar ratio of the number of moles of the electrolytic salt to the total number of moles of ether oxygen atoms in the oxyalkylene groups is in a range of 0.0001 to 1.

\* \* \* \* \*